United States Patent [19]

Krämer et al.

[11] Patent Number: 4,904,682
[45] Date of Patent: Feb. 27, 1990

[54] TREATING MYCOSES WITH TRIAZOLYLALKANOLS

[75] Inventors: Wolfgang Krämer, Burscheid; Graham Holmwood, Wuppertal; Karl H. Büchel, Burscheid; Manfred Plempel, Haan, all of Fed. Rep. of Germany

[73] Assignee: Bayer Aktiengesellschaft, Leverkusen, Fed. Rep. of Germany

[21] Appl. No.: 260,082

[22] Filed: Oct. 19, 1988

[30] Foreign Application Priority Data

Oct. 30, 1987 [DE] Fed. Rep. of Germany ....... 3736747

[51] Int. Cl.$^4$ .............................................. A61K 31/41
[52] U.S. Cl. .................................................... 514/383
[58] Field of Search ........................................ 514/383

[56] References Cited

U.S. PATENT DOCUMENTS 4,734,126 3/1988 Holmwood et al. ................. 514/383

Primary Examiner—Allen J. Robinson
Attorney, Agent, or Firm—Sprung Horn Kramer & Woods

[57] ABSTRACT

A method of combating mycoses in a patient in need thereof which comprises administering to such patient an antimycotically effective amount of a triazolylalkanol of the formula

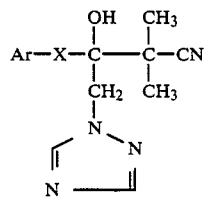

in which
  Ar stands for optionally substituted aryl and
  X stands for one of the groups —CH$_2$—; —O—CH$_2$—; —S—CH$_2$—; —CH$_2$—CH$_2$—; —CH=CH— or —C≡C—,
or a physiologically tolerable acid addition salt thereof.

8 Claims, No Drawings

TREATING MYCOSES WITH TRIAZOLYLALKANOLS invention relates to the use of new substituted triazolylalkanols for the treatment of diseases, in particular mycoses.

It has been disclosed that certain substituted triazolylalkanols, such as, for example, 3,3-dimethyl-4- fluoro-1-(4-methylphenoxy)-2-(1,2,4-triazol-1-ylmethyl)- butan-2-ol or 1-(4-chloro-2-methylphenoxy)-3,3-dimethyl4-fluoro-2-(1,2,4-triazol-1-ylmethyl)-butan-2-ol possess antimycotic properties (compare DE-OS (German Published Specification No.) 3,202,613).

However, the activity of these previously known compounds is not completely satisfactory in all indications.

It has been found that the new substituted triazolylalkanols of the general formula (I)

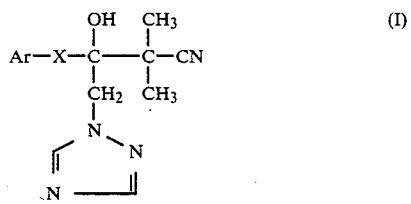

in which

Ar stands for optionally substituted aryl and

X stands for one of the groups —CH$_2$—; —O—CH$_2$—; —S—CH$_2$—; —CH$_2$—CH$_2$—; —CH=CH— or —C≡C—, and their physiologically tolerable acid addition salts possess good antimicrobial, in particular good antimycotic, properties.

The compounds of the formula (I) can exist as optical isomers or isomer mixtures of different composition. Both the use of the pure isomers and that of the isomer mixtures are claimed according to the invention.

Surprisingly, the new, substituted triazolylalkanols of the general formula (I), utilizable according to the invention, show, together with comparably good in vitro activity, a clearly better in vivo activity in certain indications than the substituted triazolylalkanols known from the prior art, such as, for example, 3,3-dimethyl-4-fluoro-1-(4-methylphenoxy)-2-(1,2,4-triazol-1-ylmethyl)- butan-2-ol or 1-(4-chloro-2-methylphenoxy)-3,3-dimethyl-4- fluoro-2-(1,2,4-triazol-1-ylmethyl)-butan-2-ol, which are structurally similar compounds.

Formula (I) provides a general definition of the substituted triazolylalkanols utilizable according to the invention. Preferably utilizable according to the invention are compounds of the formula (I), in which Ar stands for phenyl which is optionally monosubstituted or polysubstituted by identical or different substituents, suitable substituents being: halogen, in each case straight-chain or branched alkyl, alkoxy or alkylthio each having 1 to 4 carbon atoms, in each case straight-chain or branched halogenoalkyl, halogenoalkoxy or halogenoalkylthio each having 1 to 4 carbon atoms and 1 to 9 identical or different halogen atoms, in particular fluorine, chlorine and bromine and also phenyl or phenoxy each of which is optionally monosubstituted or polysubstituted by identical or different halogen, and X stands for one of the groups —CH$_2$—; —O—CH$_2$—; —S—CH$_2$—; —CH$_2$—CH$_2$—; —CH=CH— or —C≡C—.

Very particularly preferably utilizable are compounds of the formula (I), in which Ar stands for phenyl which is optionally monosubstituted, disubstituted or trisubstituted by identical or different substituents, suitable substituents being: fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, trifluoromethylthio and also phenyl or phenoxy each of which is optionally monosubstituted, disubstituted or trisubstituted by identical or different substituents from the series comprising fluorine, chlorine and/or bromine, and X stands for one of the groups —CH$_2$—; —O—CH$_2$—; —S—CH$_2$—; —CH$_2$—CH$_2$—; —CH=CH— or —C≡C—.

Preferably utilizable compounds according to the invention are also addition products of acids and those substituted triazolylalkanols of the formula (I), in which the substituents Ar and X have the meanings which have already been mentioned for these substituents.

The acids which can be adducted preferably include hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid and also saccharine or thiosaccharine.

The following substituted triazolylalkanols of the general formula (I) may be mentioned individually in addition to the compounds mentioned in the preparation examples:

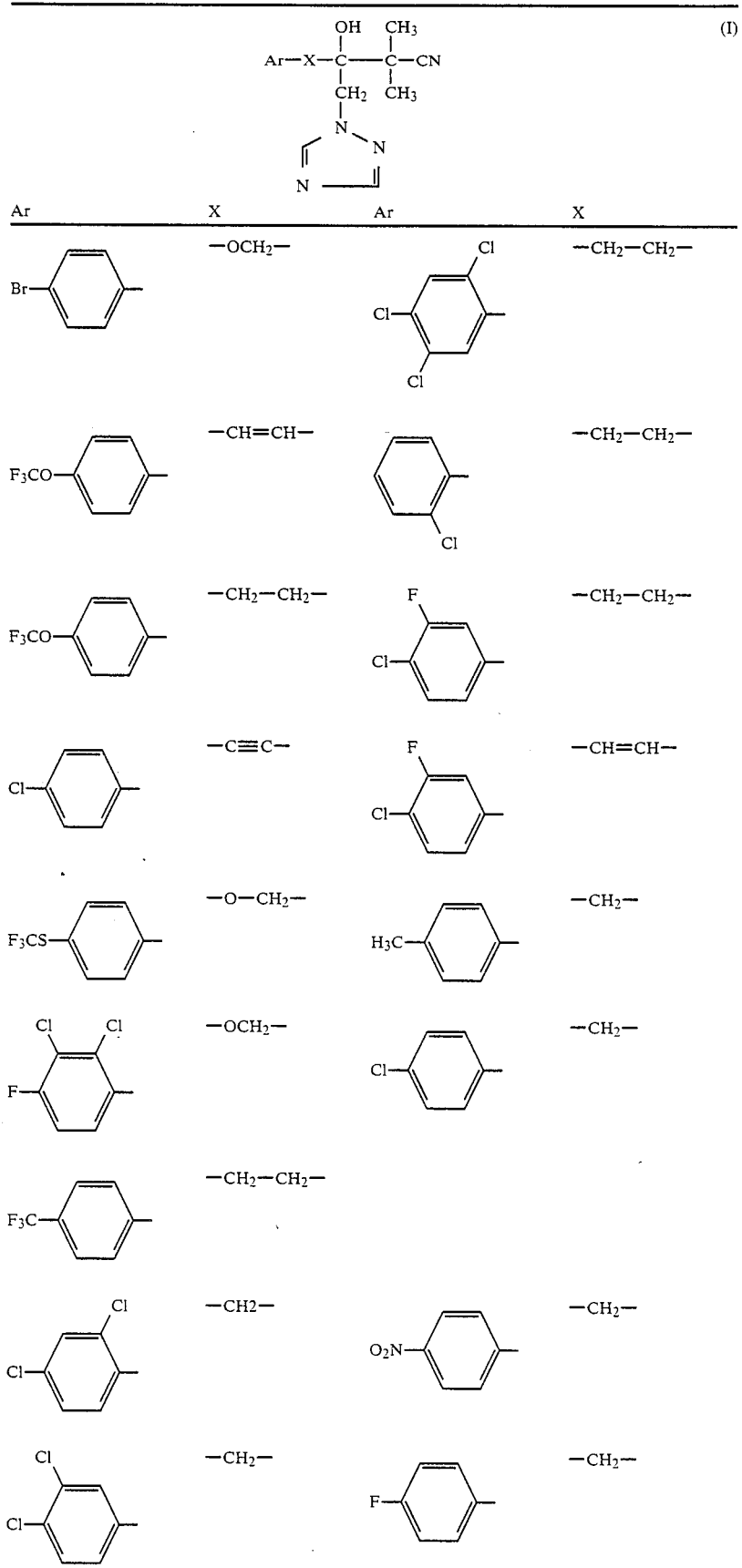

-continued

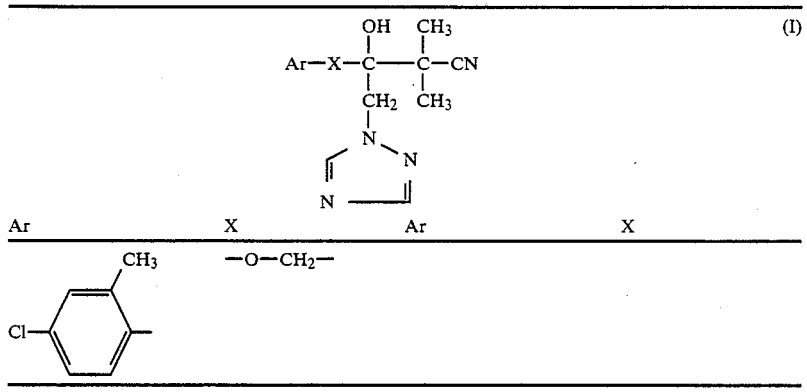

| Ar | X |
|---|---|
| 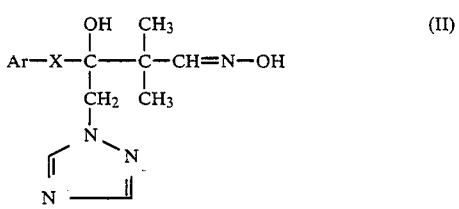 (Cl, CH3 substituted phenyl) | —O—CH2— |

The substituted triazolylalkanols of the formula (I) utilizable according to the invention and their acid addition salts are the subject of Application Serial No P 37 31 927 filed Sept. 23, 1987, now pending, and can be obtained by the process described therein, by reacting oximes of the formula (II)

$$Ar-X-\underset{\underset{\underset{N\diagdown N}{\underset{\parallel}{N}}}{CH_2}}{\overset{OH}{\underset{|}{C}}}-\overset{CH_3}{\underset{|}{C}}-CH=N-OH \quad (II)$$

in which

Ar and X have the abovementioned meaning, with a water-eliminating agent, if appropriate in the presence of a diluent and if appropriate in the presence of a reaction auxiliary, and if appropriate subsequently adducting an acid or a metal salt. If, for example, 2,2-dimethyl-3-(4-chloro-2-fluoro- benzyl)-3-hydroxy-4-(1,2,4-triazol-1-yl)-butanal oxime is used as the starting compound and acetic anhydride as the water-eliminating agent, then the course of the reaction of the preparation process can be represented by the following equation:

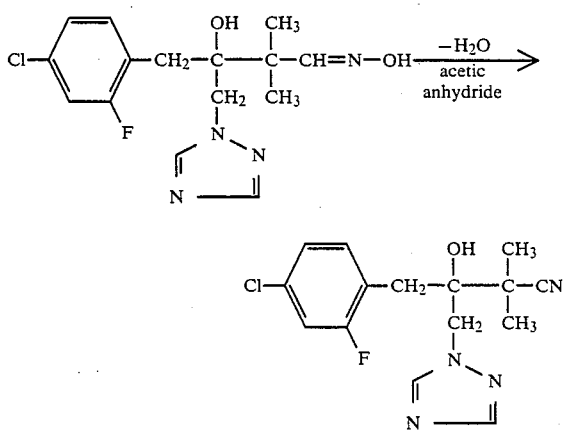

Formula (II) provides a general definition of the oximes required as starting materials for carrying out the preparation process. In this formula (II), Ar and X preferably stand for those radicals which have already been mentioned as preferred for these substituents in connection with the description of the substances of the formula (I) utilizable according to the invention.

The oximes of the formula (II) are known or can be obtained in analogy with known processes (compare DE-OS (German Published Specification) 3,334,779 and also the preparation examples).

The preparation process is carried out in the presence of a suitable water-eliminating agent. Those which are suitable are all customary dehydrating agents (compare in this respect for example C. Ferri "Reaktionen der organischen Synthese" ("Reactions of organic synthesis"), p. 572; Thieme Verlag, Stuttgart 1978). Carboxylic acid anhydrides, such as, for example, acetic anhydride are used with particular advantage.

Suitable diluents for carrying out the preparation process are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether or esters, such as ethyl acetate.

It is also possible when using liquid, water-eliminating agents to employ these in an appropriate excess simultaneously as a diluent.

The preparation process is optionally carried out in the presence of a suitable reaction auxiliary. Those which are suitable are inorganic or organic bases. These include, for example, carbonates or acetates of alkali metals, such as sodium carbonate, sodium acetate, potassium carbonate or sodium hydrogen carbonate, and also tertiary amines, such as triethylamine, N,N-dimethylaniline, pyridine or N,N-dimethylaminopyridine.

However, it is also possible to carry out the preparation process without addition of a reaction auxiliary.

The reaction temperatures can be varied within a relatively wide range when carrying out the preparation process. In general, the process is carried out at temperatures between 0° C. and 120° C., preferably at temperatures between 40° C. and 110° C.

When carrying out the preparation process, in general 1.0 to 50.0 mols, preferably 1.0 to 10.0 mols, of water-eliminating agent and if appropriate 1.0 to 5.0 mols, preferably 1.0 to 2.5 mols, of reaction auxiliary are employed per mol of oxime of the formula (II). The reaction is carried out, and the reaction products are worked up and isolated by generally customary methods.

The following acids are preferably suitable for the preparation of physiologically tolerable acid addition salts of the compounds of the formula (I): hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid and also saccharine or thiosaccharine.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and can be isolated in a known manner, for example by filtering off, and if appropriate can be purified by washing with an inert organic solvent.

The compounds of the formula (I), utilizable according to the invention, and their acid addition salts exhibit antimicrobial, in particular strong antimycotic, actions. They possess a very wide spectrum of antimycotic action, in particular against Dermatophytes and Blastomyces and also biphasic fungi, for example against Candida species, such as Candida albicans, Epidermophyton species, such as *Epidermophyton floccosum*, Aspergillus species, such as *Aspergillus niger* and *Aspergillus fumigatus*, Trichophyton species, such as *Trichophyton mentagrophytes*, Microsporon species, such as *Microsporon felineum* and also Torulopsis species, such as *Torulopsis glabrata*. The enumeration of these microorganisms in no case represents a limitation of the controllable bacteria, but is only of illustrative character.

Indication examples in human medicine which may be mentioned are, for example:

Dermatomycoses and systemic mycoses produced by *Trichophyton mentagrophytes* and other Trichophyton species, Microsporon species and also *Epidermophyton floccosum*, Blastomyces and biphasic fungi and also Hyphomycetes.

Indication areas in animal medicine which may be mentioned are, for example:

All dermatomycoses and systemic mycoses, in particular those which are produced by the abovementioned pathogens.

The present invention includes pharmaceutical preparations which contains one or more active compounds according to the invention in addition to non-toxic, inert pharmaceutically suitable excipients or which consist of one or more active compounds according to the invention.

The present invention also includes pharmaceutical preparations in dosage units. This means that the preparations are present in the form of individual portions, for example tablets, dragees, capsules, pills, suppositories and ampoules, whose active compound content corresponds to a fraction or a multiple of an individual dose. The dosage units may contain, for example, 1, 2, 3 or 4 individual doses or $\frac{1}{2}$, $\frac{1}{3}$ or $\frac{1}{4}$ of an individual dose. An individual dose preferably contains the amount of active compound which is administered in one application and which usually corresponds to a whole, a half or a third or a quarter of a daily dose.

Non-toxic, inert pharmaceutically suitable excipients are taken to mean solid, semisolid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powder or sprays.

Tablets, dragees, capsules, pills and granules may contain the active compounds(s) in addition to the customary excipients, such as (a) fillers and extenders, for example starches, lactose, sucrose, glucose, mannitol and silicic acid, (b) binders, for example carboxymethylcellulose, alginates, gelatin, polyvinylpyrrolidone, (c) humectants, for example glycerol, (d) disintegrants, for example agar-agar, calcium carbonate and sodium bicarbonate, (e) solution retarders, for example paraffin and (f) absorption accelerators, for example quaternary ammonium compounds, (g) wetting agents, for example cetyl alcohol, glycerol monostearate, (h) adsorbants, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be provided with the customary coatings and shells containing, if appropriate, opacification agents and may be composed so that they release the active compound(s) only or preferably in a certain part of the intestinal tract, if appropriate in a delayed manner, where, for example, polymeric substances and waxes may be used as embedding materials.

The active compound(s) may, if appropriate, also be present in microencapsulated form with one or more of the abovementioned excipients.

Suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances in addition to the active compound(s).

Ointments, pastes, creams and gels may contain the customary excipients, for example animal and vegetable fats, waxes, paraffins, starches, tragacanth, cellulose derivatives, polyethylene glycols, silicones, bentonites, silicic acid, talc and zinc oxide or mixtures of these substances in addition to the active compound(s).

Powder and sprays may contain the customary excipients, for example lactose, talc, silicic acid, aluminium hydroxide, calcium silicate and polyamide powder or mixtures of these substances, and sprays may additionally contain the customary propellants, for example chlorofluorohydrocarbons, in addition to the active compound(s).

Solutions and emulsions may contain the customary excipients such as solvents, solution retarders and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propyl alcohol, suspending agents, for example ethoxylated isostearyl alcohols, polyoxyethylene sorbitol, esters and polyoxyethylene sorbitan esters, microcrystalline cellulose, aluminum metahydroxide, bentonite, agar-agar and tragacanth or mixtures of these substances in addition to the active compound(s).

The said formulation forms may also contain colorants, preservatives and also odour-improving and flavour-improving additives, for example peppermint oil and eucalyptus oil and sweeteners, for example saccharine.

The therapeutically active compounds should be present in the abovementioned pharmaceutical preparations preferably in a concentration from about 0.1 to 99.5, preferably from 0.5 to 95% by weight, of the total mixture.

The abovementioned pharmaceutical preparations can also contain further pharmaceutical active compounds in addition to the active compounds according to the invention.

The preparation of the abovementioned pharmaceutical preparations takes place in a customary manner by known methods, for example by mixing the active compound(s) with the excipient(s).

The present invention also includes the use of the active compounds according to the invention, and also of pharmaceutical preparations which contain one or more active compounds according to the invention in human and veterinary medicine for prophylaxis, amelioration and/or cure of the abovementioned diseases.

The active compounds or the pharmaceutical preparations may be administered locally, orally, parenterally, intraperitoneally and/or rectally, preferably parenterally, in particular intravenously.

In general, it has proved advantageous in both human and veterinary medicine to administer the active compound(s) according to the invention in total amounts of about 2.5 to about 200, preferably from 5 to 150 mg/kg of body weight every 24 hours, if appropriate in the form of several individual doses to obtain the desired results.

For oral applications, the active compounds according to the invention are administered in total amounts of about 2.5 to about 200, preferably from 5 to 150 mg/kg of body weight every 24 hours and for parenteral administration in total amounts from about 2.5 to about 50, preferably from 1 to 25 mg/kg of body weight every 24 hours.

However, it may be necessary to deviate from the said dosages, depending on the species and the body weight of the object to be treated, the nature and severity of the disease, the type of the preparation and the administration of the medicament and also the time period or interval within which the administration takes place. Thus, in some cases it is sufficient to manage with less than the abovementioned amount of active compound, whereas in other cases the abovementioned amount of active compound must be exceeded. It is possible for anyone skilled in the art to establish the optimum dosage necessary in each case and the type of application of the active compound on the basis of his expert knowledge.

PREPARATION EXAMPLES

Example 1:

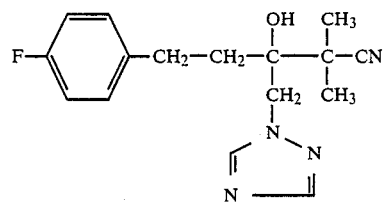

16 g (0.05 mol) of 2,2-dimethyl-5-(4-fluorophenyl)3-hydroxy-3-(1,2,4-triazol-1-ylmethyl)-pentanal oxime are heated to reflux temperature for 3 hours in 150 ml of acetic anhydride, cooled and poured onto 200 g of ice, and the mixture is extracted using 300 ml of dichloromethane, dried over sodium sulphate and concentrated in vacuo. The residue is brought to crystallization by stirring with 150 ml of diethyl ether, and the crystals are filtered off with suction and dried.

11 g (73% of theory) of 5-(4-fluorophenyl)-3- hydroxy-2-methyl-3-(1,2,4-triazol-1-ylmethyl)pentane 2carbonitrile of melting point 152°–154° C. are obtained.

Preparation of the starting compound

Example II-1

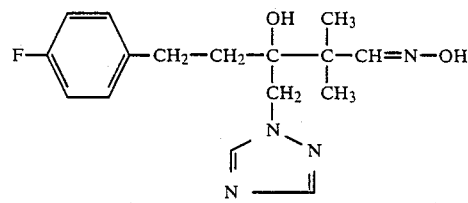

41.2 g (0.135 mol) of 2,2-dimethyl-5-(4-fluoro- phenyl)-3-hydroxy-3-(1,2,4-triazol-1-ylmethyl)pentanal and 11.1 g (0.16 mol) of hydroxylamine hydrochloride are heated under reflux for 6 hours in 300 ml of ethanol, cooled, poured into 1,000 ml of saturated aqueous sodium hydrogen carbonate solution and the mixture is extracted twice with 300 ml of dichloromethane each time. The combined organic phases are washed twice with 400 ml of water each time, dried over sodium sulphate and concentrated in vacuo. The residue is recrystallized from diisopropyl ether.

30 g (70% of theory) of 2,2-dimethyl-5-(4-fluorophenyl)-3-hydroxy-3-(1,2,4-triazol-1-ylmethyl)pentanal oxime of melting point 101° C. to 103° C. are obtained.

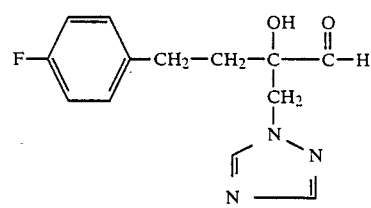

85 mo of concentrate hydrochloric acid are added to 124 g (0.355 mol) of 2-(1,3-dioxlan-2-yl)-5-(4-fluorophenyl)-2-methyl-3-(1,2,-triazol-1-ylmethyl)-pentan-3- ol in a mixture of 850 ml of ethanol and 850 ml of water, the mixture is stirred at room temperature for 16 hours and concentrated in a water-jet vacuum to half its volume, neutralized using aqueous sodium bicarbonate solution and extracted using 600 ml of dichloromethane, and the combined organic phases are washed with 1,500 ml of water, dried over sodium sulphate and concentrated in vacuo. The residue is taken up in 600 ml of acetone, 48 g of 1,8-naphthalenedisulphonic acid in 80 ml of acetone are added at 0° C. and the mixture is stirred at this temperature for 4 hours; the resultant precipitate is filtered off with suction and stirred into 2,500 ml of saturated aqueous sodium bicarbonate solution. The mixture is extracted several times with a total of 600 ml of dichloromethane, dried over sodium sulphate and concentrated in vacuo, and the residue is recrystallized from diisopropyl ether.

64 g (59% of theory) of 2,2-dimethyl-5-(4-fluorophenyl)-3-hydroxy-3-(1,2,4-triazol-1-ylmethyl)-pentanal of melting point 98° C. are obtained.

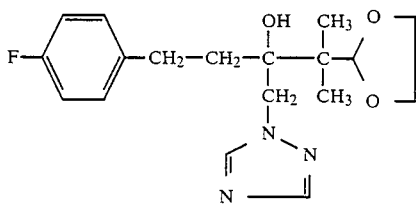

2.3 g of powdered potassium hydroxide are added to 193 g (about 0.41 mol) of crude 2-[2-(1,3-dioxolan-2-yl)-prop-2-yl]-2-[2-(4-fluorophenyl)-ethyl]oxirane (about 60% purity in 600 ml of n-butanol and the mixture is heated to reflux temperature for 16 hours. For working up, the mixture is concentrated in vacuo, the residue is taken up in 700 ml of dichloromethane, washed twice with 1,500 ml of water each time, dried over sodium sulphate and concentrated in vacuo, and the residue is chromatographed over silica gel (eluant: cyclohexane/ethyl acetate 4:1).

124 g (86% of theory) of 2-(1,3-dioxolan-2-yl)-5(4-fluorophenyl)-2-methyl-3-(1,2,4-triazol-1-ylmethyl)-pentan-3-ol are obtained as an oil.

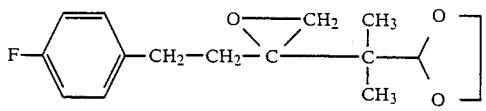

170.4 g (1.2 mols) of methyl iodide are added dropwise with stirring to 74.4 g (1.2 mols) of dimethyl sulphide in 350 ml of absolute dimethyl sulphoxide and 200 ml of absolute tetrahydrofuran, the mixture is stirred at room temperature for 16 hours, then 190 g (0.7 mol) of 2-(1,3-dioxolan-2-yl)-5-(4-fluorophenyl)-2-methyl-pentan-3-one in 300 ml of toluene are added dropwise with stirring and then 40 g (0.7 mol) of sodium methoxide are added at 5° C. in 3 portions during a time period of 90 minutes, the mixture is stirred for a further 3 hours at room temperature, then a further 30 g (0.55 mol) of sodium methoxide are added at 5° C. in 2 portions within the course of 30 minutes, the mixture is stirred at 20° C. for 10 hours and at 45° C. for a further 8 hours and concentrated in vacuo, and the residue is taken up in 1,000 ml of dichloromethane, washed 3 times with 1,000 ml of water each time, dried over sodium sulphate and concentrated in vacuo.

193 g (about 60% of theory) of crude 2-[2-(1,3- dioxolan-2-yl)-prop-2-yl]-2-[2-(4-fluorophenyl)-ethyl]oxirane are obtained in about 60% purity, which can be employed without additional purification steps in the next stage.

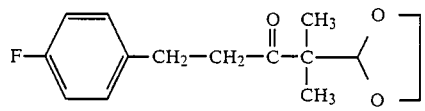

193 g (0.73 mol) of 2-(1,3-dioxolan-2-yl)-5-(4- fluorophenyl)-2-methyl-pent-4-en-3-one in 1,200 ml of tetrahydrofuran are hydrogenated for 7 hours at 31° C. and a hydrogen pressure of 55 bar in the presence of 20 g of Raney nickel. For working up, the catalyst is filtered off and the solvent is removed by distillation.

190 g (99% of theory) of 2-(1,3-dioxolan-2-yl)-5(4-fluorophenyl)-2-methyl-pentan-3-one are obtained as an oil, which according to gas chromatographic analysis is present in 97% purity.

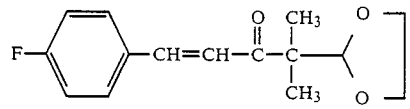

84 ml of 10% strength aqueous sodium hydroxide solution are added dropwise with stirring to 124 g (1 mol) of 4-fluorobenzaldehyde and 158 g (1 mol) of 2-(1,3-dioxolan- 2-yl)-2-methyl-butan-3-one (compare, for example, DE-OS (German Published Specification) No. 3,242,252 or DE-OS (German Published Specification) No. 3,242,236) in 350 ml of ethanol and 124 ml of water, and the mixture is stirred for a further 16 hours at room temperature after completion of the addition, and the precipitated solid is filtered off with suction and then washed using a little ethanol.

206 g (78% of theory) of 2-(1,3-dioxolan-2-yl)-5(4-fluorophenyl)-2-methyl-pent-4-en-3-one of melting point 76° C. are obtained, which can be recrystallized from petroleum ether.

The following substituted triazolylalkanols of the general formula (I)

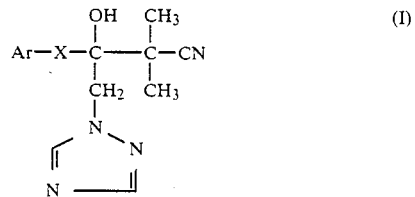

are obtained in a corresponding manner and according to the general instructions for preparation:

| Example No. | Ar | X | Physical constants |
|---|---|---|---|
| 2 | Cl—⟨⟩— | —CH$_2$—CH$_2$— | m.p.: 141° C. |

-continued

| Example No. | Ar | X | Physical constants |
|---|---|---|---|
| 3 | 2,4-dichlorophenyl | —CH$_2$—CH$_2$— | m.p.: 102–104° C. |
| 4 | 4-bromophenyl | —S—CH$_2$— | $^1$H—NMR*: 3.24 (q); 4.58 (q) |
| 5 | 4-chlorophenyl | —S—CH$_2$— | $^1$H—NMR*: 3.23 (q); 4.56 (q) |
| 6 | 2,4-dichlorophenyl | —O—CH$_2$— | m.p.: 130–132° C. |
| 7 | biphenyl | —O—CH$_2$ | $^1$H—NMR*: 3.72 (q); 4.71 (q) |
| 8 | 4-chlorophenyl | —O—CH$_2$— | m.p.: 120–122° C. |
| 9 | 2,4-difluorophenyl | —CH$_2$—CH$_2$— | m.p.: 133–135° C. |
| 10 | 4-chloro-2-fluorophenyl | —CH$_2$—CH$_2$— | m.p.: 123° C. |
| 11 | 2-chloro-4-fluorophenyl | —O—CH$_2$— | m.p.: 133–135° C. |
| 12 | 4-fluorophenyl | —S—CH$_2$— | $^1$H—NMR*: 3.2 (q); 4.55 (q) |

*The $^1$H—NMR spectra were recorded in deuterochloroform (CDCl$_3$) using tetramethylsilane (TMS) as the internal standard. The chemical shift is given as δ value in ppm.

USE EXAMPLES

The compounds shown below were employed as comparison substances in the following use examples:

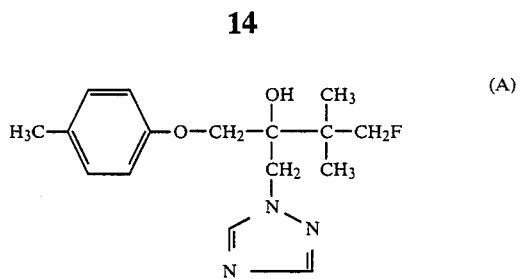

3,3-Dimethyl-4-fluoro-1-(4-methylphenoxy)-2-(1,2,4-triazol-1-methyl)-butan-2-ol (known from DE-OS (German Published Specification) No. 3,202,613)

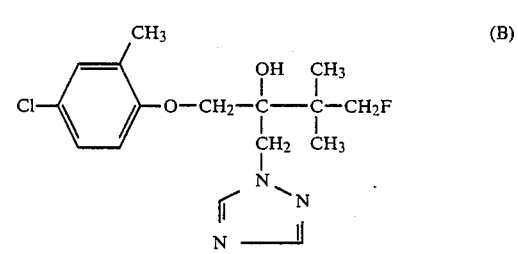

1-(4-Chloro-2-methylphenoxy)-3,3-dimethyl-4-fluoro2-(1,2,4-triazol-1-ylmethyl)-butan-2-ol (known from DE-OS (German Published Specification) No. 3,202,613)

Example A

Antimycotic in Vitro Activity

Experimental Description

The in vitro tests were carried out in a serial dilution test using bacterial inocula of, on average, $5 \times 10^3$ to $10^4$ bacteria/ml of substrate. Nutrients used were (a) for Dermatophytes and Hyphomycetes: Sabouraud's test medium (b) for yeasts: meat extract/dextrose broth.

The incubation temperature was 28° C. to 37° C., and the incubation period was 24 to 96 hours for yeasts and 96 hours for Dermatophytes and Hyphomycetes.

In this test, for example, the compounds 2, 4, 5, 7 and 10 utilizable according to the invention show good antimycotic activity, as seen in Table A.

TABLE A

Antimycotic in vitro activity

| active compound | MIC* values in μg/ml of nutrient medium | | | | |
|---|---|---|---|---|---|
| | Trichophyton mentagr. | Microsporum canis | Candida albicans | Torulopsis glabrata | Aspergillus fumigatus |
| (2) | <1 | 16 | 16 | 16 | 16 |

TABLE A-continued

Antimycotic in vitro activity

| | MIC* values in μg/ml of nutrient medium | | | | |
|---|---|---|---|---|---|
| active compound | Tricho- phyton mentagr. | Micro- sporum canis | Candida albi- cans | Toru- lopsis gla- brata | Asper- gillus fumi- gatus |
| (4) Br–C₆H₄–S–CH₂–C(OH)(CH₂-triazole)–C(CH₃)₂–CN | <1 | 16 | 8 | 8 | 4 |
| (5) Cl–C₆H₄–S–CH₂–C(OH)(CH₂-triazole)–C(CH₃)₂–CN | 8 | — | 4 | 4 | 8 |
| (7) biphenyl–O–CH₂–C(OH)(CH₂-triazole)–C(CH₃)₂–CN | <1 | <1 | 2 | 16 | 2 |
| (10) 4-Cl-2-F-C₆H₃–CH₂–CH₂–C(OH)(CH₂-triazole)–C(CH₃)₂–CN | 2 | — | 8 | 16 | 16 |

*minimum inhibitory concentration

Example B

Antimycotic in vivo activity (oral) in mouse candidiasis

Experimental description

Mice of the SPF-CF$_1$ type are intravenously inoculated with $1$–$2 \times 10^6$ logarithmically growing Candida cells, which have been suspended in physical logical saline solution. One hour before and seven hours after infection, the animals are orally treated with 25–100 mg/kg of body weight of the preparation in each case.

Result Untreated animals died 3 to 6 days post infection. The survival rate on the 6th day post infection was about 5% in untreated control animals.

In this test, for example, the compound (8) utilizable according to the invention shows a better action than the compounds (A) and (B) known from the prior art, as seen in Table B.

TABLE B

Antimycotic in vivo action (oral) in mouse candidiasis

| Active compound | Action |
|---|---|
| (A) (known) H₃C–C₆H₄–O–CH₂–C(OH)(CH₂-triazole)–C(CH₃)(CH₂F)–CH₃ | n.a. |
| (B) (known) 4-Cl-2-CH₃-C₆H₃–O–CH₂–C(OH)(CH₂-triazole)–C(CH₃)(CH₂F)–CH₃ | + |

TABLE B-continued

Antimycotic in vivo action (oral) in mouse candidiasis (8) ++++

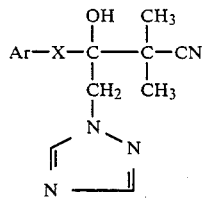

Explanation of symbols:

| | |
|---|---|
| +++++ = very good action | = 90% survival on the 6th day post infection |
| ++++ = good action | = 80% survival on the 6th day post infection |
| +++ = action | = 60% survival on the 6th day post infection |
| ++ = weak action | = 40% survival on the 6th day post infection |
| + = trace action | = under 40% survival on the 6th day post infection |
| n.a. | = no difference to untreated infection control |

Example C/Formulations (1.) Solution:

| | |
|---|---|
| Active compound according to formula (I): | 10 g |
| Alcohol, pure (96% strength): | 300 g |
| Isopropyl myristate: | 526 g |
| | 836 g |

(2.) Cream:

| | |
|---|---|
| Active compound according to formula (I): | 10 g |
| Arlacel 60: (sorbitan monostearate) | 20 g |
| Tween 60: (polyoxyethylene (20) sorbitan monostearate) | 15 g |
| Spermaceti, synthetic: (mixture of esters of $C_{14}$–$C_{18}$ saturated fatty acids and $C_{14}$–$C_{18}$ fatty alcohols) | 30 g |
| Lanette 0: (mixture of cetyl alcohol and stearyl alcohol) | 100 g |
| Eutanol G: (2-octyldodecanol) | 135 g |
| Benzyl alcohol: | 10 g |
| Water, demineralized: | 680 g |
| | 1000 g |

It will be appreciated that the instant specification and claims are set forth by way of illustration and not limitation, and that various modifications and changes may be made without departing from the spirit and scope of the present invention.

What is claimed is:

1. A method of combating mycoses in a partner in need thereof which comprises administering to such patient an antimycotically effective amount of a triazolylalkanol of the formula $$Ar-X-\underset{\underset{\underset{N\diagdown N}{\overset{|}{CH_2}}}{\overset{|}{\underset{|}{C}}}}{\overset{OH}{\overset{|}{C}}}-\underset{CH_3}{\overset{CH_3}{\overset{|}{C}}}-CN$$

in which
Ar stands for phenyl which is optionally monosubstituted or polysubstituted by identical or different substituents selected from the group consisting of halogen, in each case straight-chain or branched alkyl, alkoxy or alkylthio each having 1 to 4 carbon atoms, in each case straight-chain or branched halogenoalkyl, halogenoalkoxy or halogenoalkylthio each having 1 to 4 carbon atoms and 1 to 9 identical or different halogen atoms, and phenyl or phenoxy each of which is optionally monosubstituted or polysubstituted by identical or different halogen, and
X stands for one of the groups —$CH_2$—; —O—$CH_2$—; —S—$CH_2$—; —$CH_2$—$CH_2$—; —CH=CH— or —C≡C—, or a physiologically tolerable acid addition salt thereof.

2. The method according to claim 1, in which Ar stands for phenyl which is optionally monosubstituted, disubstituted or trisubstituted by identical or different substituents selected from the group consisting of fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, trifluoromethylthio and phenyl or phenoxy each of which is optionally monosubstituted, disubstituted or trisubstituted by identical or different substituents selected from the group consisting of fluorine, chlorine and bromine.

3. The method according to claim 1, wherein such compound is 5-(4-chlorophenyl)-3-hydroxy-2-methyl-3-(1,2,4- triazolyl-1-ylmethyl)-pentane 2-carbonitrile of the formula

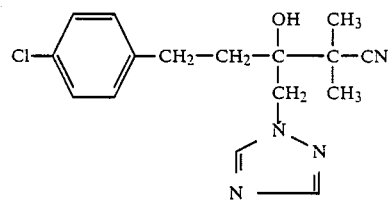

or a physiologically tolerable acid addition salt thereof.

4. The method according to claim 1, wherein such compound is 4-(4-bromophenylthio)-3-hydroxy-2-methyl3-(1,2,4-triazolyl-1-ylmethyl)-butane 2-carbonitrile of the formula

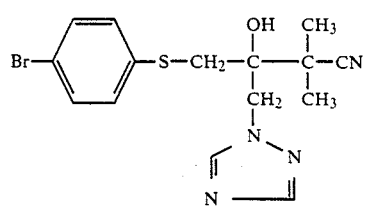

or a physiologically tolerable acid addition salt thereof.

5. The method according to claim 1, wherein such compound is 4-(4-chlorophenylthio)-3-hydroxy-2-methyl 3-(I,2,4-triazolyl-1-ylmethyl)-butane 2-carbonitrile of the formula

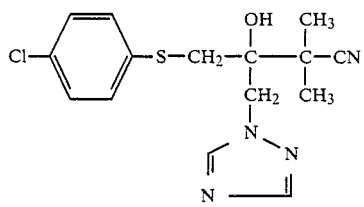

or a physiologically tolerable acid addition salt thereof.

6. The method according to claim 1, wherein such compound is 1-(4-biphenyloxy)-2-hydroxy-3-methyl-2(1,2,4-triazolyl-1-ylmethyl)-butane 3-carbonotrile of the formula

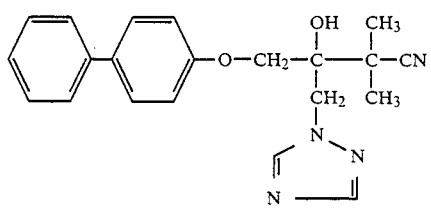

or a physiologically tolerable acid addition salt thereof.

7. The method according to claim 1, wherein such compound is 1-(4-chlorophenoxy)-2-hydroxy-3-methyl-2(1,2,4-triazolyl-1-ylmethyl)-butan 3-carbonitrile of the formula

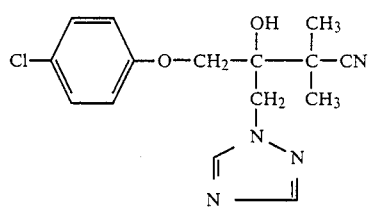

or a physiologically tolerable acid addition salt thereof.

8. The method according to claim 1, wherein such compound is 5-(4-chloro-2-fluorophenyl)-3-hydroxy-2 methyl-3-(1,2,4-triazolyl-1-ylmethyl)-pentane 2-carbonitrile of the formula

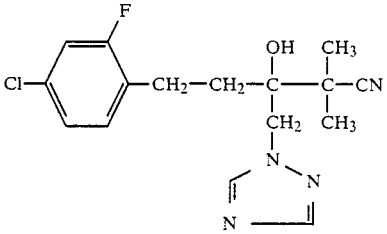

or a physiologically tolerable acid addition salt thereof.

* * * * *